United States Patent
Stypulkowski

(10) Patent No.: US 7,286,878 B2
(45) Date of Patent: Oct. 23, 2007

(54) MULTIPLEXED ELECTRODE ARRAY EXTENSION

(75) Inventor: Paul Stypulkowski, N. Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 254 days.

(21) Appl. No.: 10/045,122

(22) Filed: Nov. 9, 2001

(65) Prior Publication Data

US 2003/0093130 A1  May 15, 2003

(51) Int. Cl.
*A61N 1/08* (2006.01)

(52) U.S. Cl. .............................. 607/37; 607/38; 607/9; 607/2; 607/15

(58) Field of Classification Search .................. 607/2, 607/4, 9, 15, 27, 30, 43, 50, 62, 117, 148, 607/37, 38; 600/373, 522
See application file for complete search history.

(56) References Cited

U.S. PATENT DOCUMENTS

| | | | |
|---|---|---|---|
| 4,399,820 A * | 8/1983 | Wirtzfeld et al. ............. | 607/21 |
| 4,595,009 A | 6/1986 | Leinders | |
| 4,628,934 A * | 12/1986 | Pohndorf et al. ............. | 607/27 |
| 4,791,935 A | 12/1988 | Baudino et al. | |
| 4,877,032 A * | 10/1989 | Heinze et al. ................. | 607/2 |
| 4,969,463 A * | 11/1990 | Dahl et al. ...................... | 607/5 |
| 5,178,161 A | 1/1993 | Kovacs | |
| 5,275,171 A | 1/1994 | Barcel | |
| 5,281,219 A | 1/1994 | Kallok | |
| 5,314,495 A | 5/1994 | Kovacs | |
| 5,336,253 A | 8/1994 | Gordon et al. | |
| 5,411,532 A | 5/1995 | Mortazavi | |
| 5,423,873 A * | 6/1995 | Neubauer et al. ............. | 607/68 |
| 5,537,156 A | 7/1996 | Katayama | |
| 5,782,891 A | 7/1998 | Hassler et al. | |
| 5,843,135 A | 12/1998 | Weijand et al. | |
| 5,935,155 A | 8/1999 | Humayun et al. | |
| 5,999,848 A | 12/1999 | Gord et al. | |
| 6,038,480 A | 3/2000 | Hrdlicka et al. | |
| 6,418,348 B1 * | 7/2002 | Witte ......................... | 607/122 |
| 6,473,653 B1 | 10/2002 | Schallhorn et al. | |

FOREIGN PATENT DOCUMENTS

| | | |
|---|---|---|
| EP | 1040848 A1 | 10/2000 |
| WO | WO87/07825 | 12/1987 |
| WO | WO97/37720 A | 10/1997 |
| WO | WO99/06105 A | 2/1999 |
| WO | WO99/45870 A1 | 9/1999 |

OTHER PUBLICATIONS

PCT International Search Report PCT/US02/09887 (Mailed Aug. 8, 2002).

* cited by examiner

*Primary Examiner*—Kennedy J. Schaetzle
(74) *Attorney, Agent, or Firm*—Stephen W. Bauer; Rick L. franzen

(57) ABSTRACT

An apparatus and method for selectively interacting with electrically excitable tissue of a patient are provided. The apparatus includes an implantable pulse generator having a number of output sources that transmit pulse signals. An extension unit couples the implantable pulse generator to an implantable electrode array. The implantable electrode array has a number of electrodes, wherein the number of electrodes is greater than the number of output sources. The extension unit is configured to electrically connect the output sources to a portion of the electrodes.

34 Claims, 3 Drawing Sheets

//MULTIPLEXED ELECTRODE ARRAY EXTENSION

FIELD OF THE INVENTION

The present invention relates to the field of implantable systems for stimulating electrically excitable tissue within a patient. More specifically, the present invention provides a system that includes an extension unit that connects an implantable pulse generator to an implantable lead or electrode array.

BACKGROUND OF THE INVENTION

Electrical stimulation of the spinal cord and deep brain has been used for pain relief and to control movement disorders. Electrical leads having many electrodes are implanted in the body such that one or more cathodes and one or more anodes are in optimal locations to produce benefits or to minimize undesirable side effects. FIG. 1 shows a typical implantable electrical stimulation system. An implantable pulse generator 10 generates the electrical signals that will provide the stimulation. A cable 20 connects the implantable pulse generator 10 to a lead 30. Lead 30 contains individual electrodes 31-40. Cable 20 contains ten separate conductors connecting the implantable pulse generator to each of the electrodes 31-40. Implantable electrical stimulation systems are described in co-pending patent application Ser. No. 09/024,162 filed Feb. 17, 1998 and co-pending patent application Ser. No. 08/627,576 filed Apr. 4, 1996. The entire disclosures of both co-pending applications are incorporated herein by reference.

It would be desirable to use a lead with a large number of electrodes, such as sixteen or more, for some therapies. The polarity of each electrode could be assigned and the optimal combinations of cathodes and anodes could be selected for each patient. Another advantage to having several electrodes is that it allows for adjusting the stimulation after the components have been implanted. In particular, an implanted spinal cord stimulation lead can shift up to 0.5 cm or more after being inserted in the body. Ideally, the lead should contain enough electrodes so that some electrodes can be switched off and others switch on after the shift has taken place to avoid the patient undergoing another surgical procedure. It may also be desirable to change the location of the stimulation after the lead has been implanted.

The use of a large number of electrodes on a lead has been limited, in part, because of the limitations imposed by the conductors that connect the implantable pulse generator to the lead. Typical implantable electrical stimulation systems pass up to 20 milliamperes or more of current through each conductor, involving current densities of 10 microcoulombs per square centimeter per phase or more. As a result, each electrode is connected to a sizable conductor in order to minimize energy losses due to impedance and to provide adequate strength to connect the wire to a power supply without substantial risk of breakage. The size of the conductors has made it impractical to connect a large number of conductors between the implantable pulse generator and the electrodes on the lead. Furthermore, it is difficult to obtain the required reliability when using a large number of conductors.

One proposed system places a semiconductor device on the lead to perform a multiplexing operation to minimize the number of conductors connecting the implantable pulse generator to the electrodes. The semiconductor increases the size of the lead and may require significant changes to the standard procedure currently used to implant leads as well as the manufacturing procedures.

Therefore, there exists a need in the art for an implantable electrical stimulation system that includes a large number of electrodes without increasing the size of the lead and that minimizes the number of conductors connecting the implantable pulse generator to the electrodes.

SUMMARY OF THE INVENTION

The present invention provides an implantable electrical stimulation system and method that includes a large number of electrodes with a reduced number of conductors connecting the implantable pulse generator to the electrodes. Minimizing the number of conductors for a given number of electrodes increases reliability and the number of electrodes that can be used.

In one embodiment, the advantages of the present invention are realized by an apparatus for selectively interacting with electrically excitable tissue of a patient. The apparatus includes an implantable pulse generator having a number of output sources that transmit electrical signals and an implantable electrode array having a number of electrodes, wherein the number of electrodes is greater than the number of output sources. An extension unit is coupled between the implantable pulse generator and the implantable electrode array and is configured to electrically connect the output sources to a portion of the electrodes.

The implantable electrode array may include at least one biomedical sensor. Furthermore, the electrodes may be arranged in a line or in a multi-dimensional array.

The advantages of the present invention may also be realized with an extension unit that electrically connects an implantable pulse generator having a number of output sources that transmit pulse signals to an implantable electrode array having a number of electrodes, wherein the number of electrodes is greater than the number of output sources. The extension unit includes an array of programmable switches, each switch being connected between one output lead and at least a portion of the electrodes. The extension unit may also include a programming logic unit, coupled to the array of programmable switches, that receives programming signals and produces signals for configuring the programmable switches.

In yet another embodiment of the invention a method of selectively providing electrical therapeutic treatment to a patient using an electrode array is provided. The method includes the steps of implanting an electrode array having a number of electrodes near electrically excitable tissue of a patient and implanting a pulse generator having a number of output electrode arrays in the patient, the number of output sources being less than the number of electrodes. An extension unit is also implanted between the electrode array and the pulse generator. The extension unit electrically connects the output sources to a portion of the electrodes. After the devices are implanted, it is determined which electrodes are physically positioned to provide optimal therapeutic treatment and the extension unit is configured to electrically couple the output sources to the electrodes identified in the determining step. Alternatively, the method may include implanting an array having a number of biomedical sensors in a patient and implanting a diagnostic device.

BRIEF DESCRIPTION OF THE DRAWINGS

The present invention is illustrated by way of example and not limited in the accompanying figures in which like reference numerals indicate similar elements and in which.

DETAILED DESCRIPTION OF PREFERRED EMBODIMENTS

Figure 1:
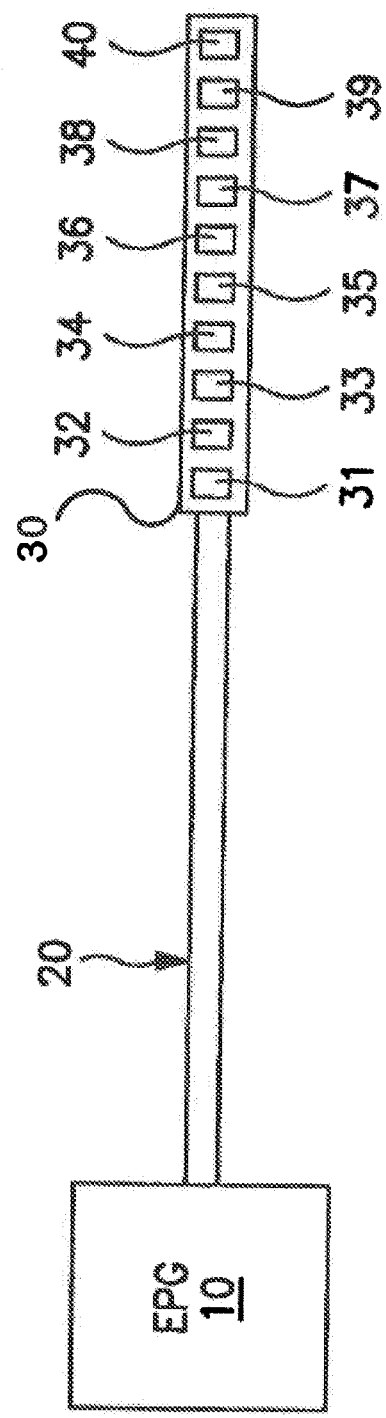
FIG. 1 shows a related art implantable electrical stimulation system.
Figure 2:
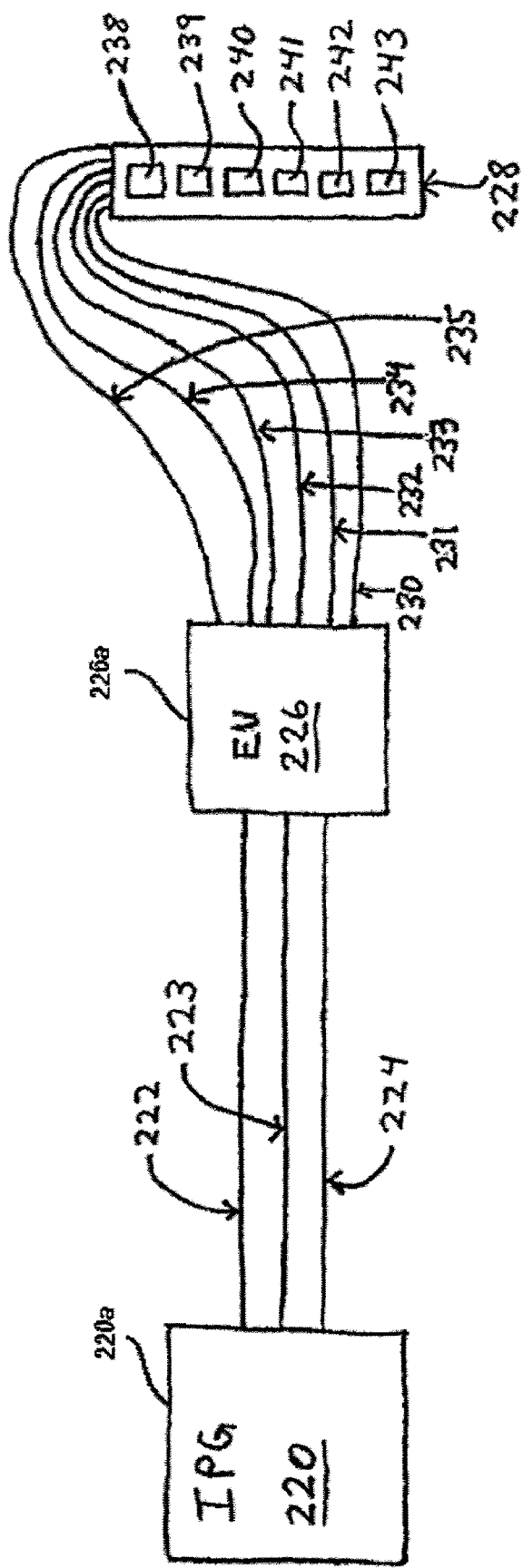
FIG. 2 is a schematic diagram of an implantable electrical stimulation system in accordance with a preferred embodiment of the invention.

FIG. 2 shows an implantable electrical stimulation system in accordance with an embodiment of the invention. An implantable pulse generator (IPG) 220 generates the stimulation signals. The structure and operation of IPGs is known to those skilled in the art. IPG 220 which includes housing 220a, is connected to extension unit 226, which includes housing 226a, with three electrical conductors 222-224. Extension unit 226 is connected to implantable electrode array 228 with six conductors 230-235. Extension unit 226 receives three electrical signals on conductors 222-224 and transmits those signals to three of conductors 230-235. FIG. 2 shows an embodiment in which extension unit 226 is located closer to implantable electrode array 228 than to IPG 220 to minimize the overall length of the conductors connecting IPG 220 to implantable electrode array 228. Extension unit 226 will be described in detail with reference to FIG. 3.

Electrode array 228 can be implanted at a site within a patient adjacent the tissue to be stimulated. Electrode array 228 has six electrodes 238-243 arranged in a straight line for illustration purposes only. Each of the electrodes 238-243 are electrically insulated from the other electrodes and can have an area of about 1-6 mm$^2$. In operation, several neighboring electrodes can be connected in parallel to have a combined surface area of 6-24 mm$^2$. Of course other sizes and configurations can be used to meet the patient's treatment needs. Electrodes 238-243 are electrically conductive and are preferably made from a metal like platinum or iridium.

Electrode array 228 can have a variety of different shapes. For example, electrode array 228 and/or electrodes 238-243 may be planar or any other shape (e.g., round, oval, and rectangular). Electrodes 238-243 also may have three dimensional outer surface (e.g., cylindrical, spherical, semi-spherical or conical). Electrode array 228 may also have any number of electrodes, such as sixteen or more and may also include one or more biomedical sensors (not shown) in place of or in addition to electrodes 238-243. A diagnostic device (not shown) may be connected to electrodes and/biomedical sensors through an extension unit that is similar to extension unit 226. Examples of diagnostic devices include glucose sensors, circuits that measure voltage levels and devices that store information. In alternative embodiment (not shown), two or more electrode arrays can be connected to a single extension unit.

Extension unit 226 allows a physician or patient to select which electrodes 238-243 will receive stimulation pulses. Being able to select and activate electrodes from a large number of possible sites provided by the preferred embodiments is valuable in case any site becomes unusable due to mechanical/electrical problems, scar tissue, electrode array migration, etc. A near neighboring site might give almost as useful a result. Furthermore, one does not always know before implantation what is the best strategy for electrode array placement and electrode polarity. Extension unit 226 allows the choice to be made later, and with additional reprogramming at later dates, to give degrees of freedom in the active electrode positions. For example, it is sometimes useful to have three or more electrodes in a line (especially transverse to the spinal cord axis), so that two or three can be chosen at preferred medial/lateral positions. The present invention enables changes in effective stimulation area after implantation by programming only while minimizing the number of conductors that connect IPG 220 to electrode array 228.

Extension unit 226 can also be used to allow the patient or physician to optimize the diagnostic function of implanted electrodes or biomedical sensors. A large number of electrodes and/or biomedical sensors can be implanted in the patient and the optimum ones can then be selected after implantation.

Figure 3:
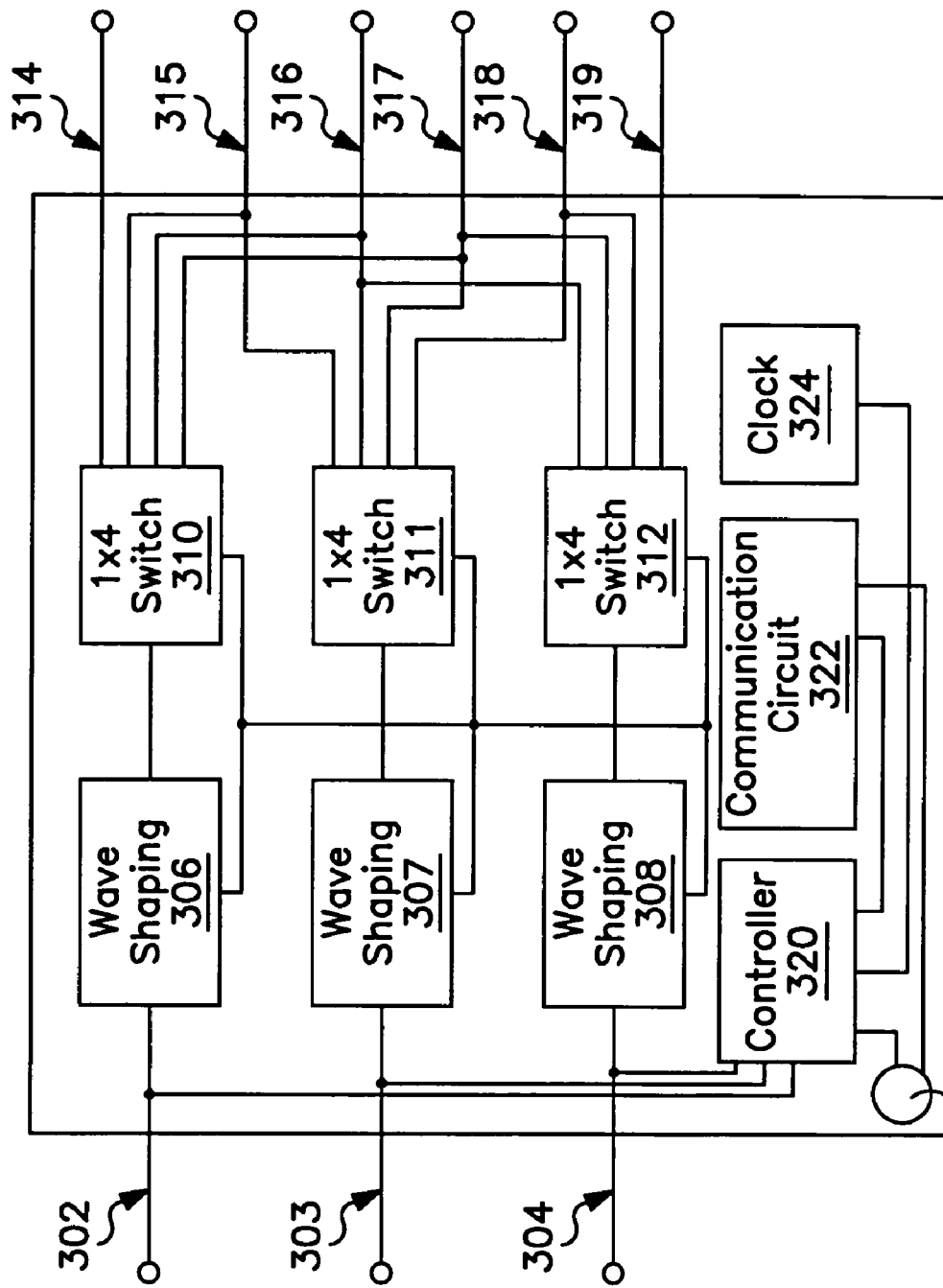
FIG. 3 is a schematic diagram of an extension unit in accordance with a preferred embodiment of the invention.

FIG. 3 illustrates a schematic diagram of an extension unit 226 in accordance with a preferred embodiment of the invention. Extension unit 226 includes input lines 302-304 that receive the input signals from the IPG 220 (shown in FIG. 2). Input lines 302-304 are connected to wave shaping circuits 306-308. Wave shaping circuits 306-308 are electrically connected to switches 310-312, which are connected to output lines 314-319. Output lines 314-319 are connected to electrode array 228 (shown in FIG. 2). Extension unit 228 may also include a controller 320 for controlling the overall operation of the unit, a communication circuit 322 for communicating with external circuits, a master clock 324 and a battery 326.

The operation of extension unit 226 will now be described. Wave shaping circuits 306-308 receive the input signals, which are generally pulses and reshapes the input signals, if necessary. Wave shaping may include changing the voltage level of the pulse or the frequency of the pulse. Wave shaping circuits 306-308 may be implemented with a variety of electrical components including potentiometers and integrated circuits. Controller 320 may receive clock signals from clock 324 and control one or more of the wave shaping circuits 306-308 to change the polarity, voltage level or frequency of the input signals.

The outputs of the wave shaping circuits 306-308 are transmitted to switches 310-312. Switches 310-312 may be implemented with a variety of electrical switches, including semiconductor switches. In one preferred embodiment, switches 310-312 are micro-relay switches that retain their switching state after power has been removed. Battery 326 may provide power to the micro-relay switches. Switches 310-312 are electrically connected to output lines 314-319.

Switches 310-312 can be configured to transmit the signals they receive to any three of output lines 314-319. Switches 310-312 can be controlled by controller 320, a source external to the body, communication circuit 322 or any combination of the three. Three input lines 302, three switches 310-312 and six output lines 314-319 are shown for illustration purposes only. Extension unit 28 can be configured to interface with any number of input lines and output lines. In one embodiment of the invention, the number of switches corresponds to the number of input lines. In the same embodiment, each switch has a number of output ports that is equal to 1+the number of output lines—the number of switches. For example, if the extension unit interfaces with five input lines and fifty output lines, the extension unit would need five 1×46 switches. Alternatively, each of the switches may be configured to be connectable to fewer of the output lines.

There are a number of conventional technologies that can be used to communicate with extension unit 226. Communication can be accomplished with needles, screwdrivers, telemetry or electromagnetic energy. In one embodiment of the invention, IPG 220 (shown in FIG. 2) can be used to program extension unit 226. In particular, input lines 302-304 are connected to controller 320. Controller 320 may include hardware or software to recognize programming signals and for programming wave shaping circuits 306-308 and/or switches 310-312. Such programming signals can include predetermined programming state pulse sequences or pulses have predetermined characteristics such as pulse length followed by programming pulses having characteristics that are recognized by controller 320. After receiving the programming signals, controller 320 can then adjust wave shaping circuits 306-308 and/or switches 310-312.

In one embodiment of the invention, extension unit 226 can be used to increase the number of electrodes that receive pulse signals. Referring to FIG. 3, wave shaping circuits 306-308 can double the voltage level and frequency of the received pulses. Switches 310-312 and then be controlled to route the signals to output lines 314-316 during a first clock period and to output lines 317-319 during a second clock period. Furthermore, the determination of which electrodes are anodes or cathodes can be chosen by the patient or through investigation by clinicians to maximize the desired effects of stimulation, e.g., maximize pain relief, minimize spasticity, stop seizures, cause contraction of muscles, etc., and also to minimize undesirable side effects. The flexibility provided by the ability to alter the shape and frequency of the input signals allows one to provide numerous types of output signals.

The invention is useful in connection with electrically excitable tissue that includes both neural tissue and muscle tissue. Neural tissue includes peripheral nerves, the spinal cord surface, the deep spinal cord, deep brain tissue and brain surface tissue. Muscle tissue includes skeletal (red) muscle, smooth (white) muscle, and cardiac muscle. Furthermore, the invention works especially well for red skeletal muscle, since stimulation on such a muscle can only activate the muscle fibers directly under the cathode. Action potentials do not spread from muscle fiber to fiber, as they do in smooth muscle or cardiac muscle. Hence, a broad array of cathodes is useful to recruit many fibers of a red muscle.

Advantageous uses for electrode array L1-L5 described in this specification include:

a. Over or in motor cortex or cerebellar cortex, where there are somatotopic maps of the body, and where fine control of the loci of excitation can help affect the movements or control of various body parts.

b. Over or in the sensory cortex, which also has a somatotopic map, so that paresthesia and/or motor effects can be adjusted to specific body parts.

c. In the thalamus, where there is a three-dimensional body map, and where there are lamina of cells that might best be activated (or partly activated) using many contacts and programming.

d. In deep tissue, where stimulation is advantageously achieved by cylindrical leads.

e. Transversely and over the cauda equina (nerves in the spinal canal descending from the tip of the cord) to enable great selectivity of stimulation.

f. In the cochlea, where there is insufficient space for many wires, but many channels are needed and where fine-tuning which sites along the cochlea get stimulated might lead to much better hearing.

g. Over branches of motor nerves or large nerves, to activate distinct fascicles.

h. In the retina, where if a patient has no light going to the back of the eye, the preferred embodiment could stimulate in neural patterns as if light were going there in focus and being perceived.

Another advantage of the invention is that allows physicians and patients to use IPGs and electrode arrays manufactured by different companies. The disclosed extension unit can be used for interfacing an IPG that was not designed to operate with a particular electrode array. One skilled in the art will appreciate that the extension unit can include additional circuits that are specifically designed to couple a particular extension unit to a particular electrode array.

While the present invention has been described in connection with the illustrated embodiments, it will be appreciated and understood that modifications can be made without departing from the true spirit and scope of the invention.

I claim:

1. An apparatus for selectively interacting with electrically excitable tissue of a patient, said apparatus comprising:
an extension unit adapted to be electrically connected to an implantable pulse generator having a number of output sources to an implantable electrode array having a number of electrodes, wherein the number of electrodes is greater than the number of output sources, the extension unit comprising:
an array of programmable switches, each switch being connected between one output source and at least a portion of the electrodes, wherein at least one switch is configured to simultaneously trigger a plurality of electrodes.

2. The extension unit of claim 1, further including:
a programming logic unit, coupled to the array of programmable switches, that receives programming signals and produces signals for configuring the programmable switches.

3. The extension unit of claim 1, wherein the array of switches comprises micro-relay switches that retain their switching state after power has been removed.

4. The extension unit of claim 1, further including an array of wave shaping circuits coupled to the array of switches and the output sources.

5. The extension unit of claim 4, wherein at least some of the wave shaping circuits are configured to change the frequency of signals received on the output sources.

6. The extension unit of claim 4, wherein at least some of the wave shaping circuits are configured to change the amplitude of signals received on the output sources.

7. The extension unit of claim 1, wherein the array of switches comprises mechanically adjustable switches.

8. The extension unit of claim 1, wherein the array of switches comprises magnetically adjustable switches.

9. An extension unit that electrically connects a distant diagnostic device having a number of input sources to an array of biomedical sensors, wherein the number of biomedical sensors is greater than the number of input sources, the extension unit comprising:
an array of programmable switches, each of the switches capable of being connected between one input source of the distant diagnostic device and at least a portion of the biomedical sensors, wherein at least one of the switches is configured to simultaneously trigger a plurality of said sensors.

10. An apparatus for selectively measuring diagnostic information from a patient, said apparatus comprising:
a diagnostic device having a number of input sources that receive electrical signals;

a lead including an implantable biomedical sensor array having a number of biomedical sensors, wherein the number of biomedical sensors is greater than the number of input sources; and an extension unit as set forth in claim 9.

11. The apparatus of claim 10, wherein a first distance between the diagnostic device and the programmable switches of the extension unit is greater than a second distance between the programmable switches of the extension unit and the biomedical sensor array.

12. An extension unit for electrically connecting an insulated set of conductors that extends from a distant housing of an implantable pulse generator having a number of output sources to a lead including an implantable electrode array having a number of electrodes, wherein the number of electrodes in the implantable electrode array is greater than the number of output sources of the implantable pulse generator, the extension unit comprising:

input lines for receiving input signals from the output sources of the distant implantable pulse generator via the set of conductors;

output lines for electrical connection with the electrodes of the implantable electrode array;

an array of programmable switches, each switch being connected between one input line and at least a portion of the output lines, wherein the switches are configured to simultaneously trigger a plurality of electrodes; and wherein the extension unit comprises an extension unit housing not in contact with the distant housing of the implantable pulse generator, whereby the extension unit enables a distant implantable pulse generator having a number of output sources to be used with a lead having an electrode array with a number of electrodes greater than the number of output sources.

13. The extension unit of claim 12, further including:

a programmable logic unit, coupled to the array of programmable switches, that receives programming signals and produces signals for configuring the programmable switches.

14. The extension unit of claim 13, wherein the array of switches comprises micro-relay switches that retain their switching state after power has been removed.

15. The extension unit of claim 14, further including an array of wave shaping circuits coupled to the array of switches and the output sources.

16. The extension unit of claim 15, wherein at least some of the wave shaping circuits are configured to change the frequency of signals received on the output sources.

17. The extension unit of claim 15, wherein at least some of the wave shaping circuits are configured to change the amplitude of signals received on the output sources.

18. The extension unit of claim 15, wherein at least some of the wave shaping circuits are configured to change the amplitude of signals received on the output sources.

19. The extension unit of claim 12, wherein the array of switches comprises micro-relay switches that retain their switching state after power has been removed.

20. The extension unit of claim 12, further including an array of wave shaping circuits coupled to the array of switches and the output sources.

21. The extension unit of claim 20, wherein at least some of the wave shaping circuits are configured to change the frequency of signals received on the output sources.

22. The extension unit of claim 21, wherein at least some of the wave shaping circuits are configured to change the amplitude of signals received on the output sources.

23. The extension unit of claim 20, wherein at least some of the wave shaping circuits are configured to change the amplitude of signals received on the output sources.

24. The extension unit of claim 12, wherein the array of switches comprises mechanically adjustable switches.

25. The extension unit of claim 12, wherein the array of switches comprises magnetically adjustable switches.

26. An apparatus for selectively interacting with electrically excitable tissue of a patient, said apparatus comprising:

an implantable pulse generator having a housing and a number of output sources that transmit electrical signals;

a lead including an implantable electrode array having a number of electrodes, wherein the number of electrodes is greater than the number of output sources;

an extension unit as set forth in claim 12; and a set of conductors for connecting the implantable pulse generator to the extension unit.

27. The apparatus of claim 26, wherein the implantable electrode array includes at least one biomedical sensor.

28. The apparatus of claim 26, wherein the electrodes are arranged in a line.

29. The apparatus of claim 26, wherein the electrodes are arranged in a multi-dimensional array.

30. The apparatus of claim 26, wherein the set of conductors are configured so that a first distance between the extension unit housing and the housing of the implantable pulse generator is greater than a second distance between the extension unit housing and the electrode array.

31. An extension unit for electrically connecting a set of conductors extending from an implantable pulse generator having a number of output sources to a lead including an implantable electrode array having a number of electrodes, wherein the number of electrodes in the implantable electrode array is greater than the number of output sources of the implantable pulse generator, the implantable pulse generator having a housing, the extension unit comprising:

a first housing, the housing not in contact with the implantable pulse generator housing;

input lines for receiving input signals from the output sources of the implantable pulse generator via the set of conductors;

output lines for electrical connection with the electrodes of the implantable electrode array; and an array of programmable switches positioned in the first housing, each switch being selectively connected between one input line and at least a portion of the output lines, wherein the switches are configured to simultaneously trigger a plurality of electrodes, whereby the extension unit enables a distant implantable pulse generator having a number of output sources to be used with a lead having an electrode array with a number of electrodes greater than the number of output sources.

32. The extension unit of claim 31, further comprising a programmable logic unit coupled to the array of programmable switches, the programmable logic unit configured to receive programming signals and produce signals for configuring the programmable switches, wherein the array of switches comprises micro-relay switches that retain their switching state after power has been removed.

33. The extension unit of claim 31, wherein the array of switches comprises micro-relay switches that retain their switching state after power has been removed.

34. The extension unit of claim 31, further including an array of wave shaping circuits coupled to the array of switches and the output sources.

* * * * *

UNITED STATES PATENT AND TRADEMARK OFFICE
CERTIFICATE OF CORRECTION

PATENT NO. : 7,286,878 B2  Page 1 of 1
APPLICATION NO. : 10/045122
DATED : October 23, 2007
INVENTOR(S) : Paul Stypulkowski It is certified that error appears in the above-identified patent and that said Letters Patent is hereby corrected as shown below:

Col. 6, line 53 (first line of claim 9): Please delete the word "distant".

Signed and Sealed this

First Day of April, 2008

JON W. DUDAS
*Director of the United States Patent and Trademark Office*